United States Patent
Koerperick et al.

(10) Patent No.: US 9,360,422 B2
(45) Date of Patent: Jun. 7, 2016

(54) NEAR-INFRARED OPTICAL PROBE AND ASSOCIATED DISPOSABLE SHEATH

(71) Applicant: ASL Analytical, Inc., Coralville, IA (US)

(72) Inventors: Edwin John Koerperick, North Liberty, IA (US); Jonathon Todd Olesberg, Iowa City, IA (US); Christine Esther Evans, North Liberty, IA (US); Mark Allen Arnold, Iowa City, IA (US); Gary Wray Small, Coralville, IA (US)

(73) Assignee: ASL Analytical, Inc., Coralville, IA (US)

( * ) Notice: Subject to any disclaimer, the term of this patent is extended or adjusted under 35 U.S.C. 154(b) by 0 days.

(21) Appl. No.: 14/709,955

(22) Filed: May 12, 2015

(65) Prior Publication Data
US 2015/0330894 A1   Nov. 19, 2015

Related U.S. Application Data

(60) Provisional application No. 61/992,735, filed on May 13, 2014.

(51) Int. Cl.
| | |
|---|---|
| *G01J 5/02* | (2006.01) |
| *G01N 21/359* | (2014.01) |
| *G01N 21/75* | (2006.01) |
| *C12M 1/34* | (2006.01) |
| *G01N 21/17* | (2006.01) |
| *G01N 21/01* | (2006.01) |
| *B01L 9/00* | (2006.01) |
| *C12Q 1/02* | (2006.01) |
| *G01N 15/14* | (2006.01) |

(Continued)

(52) U.S. Cl.
CPC ............... *G01N 21/359* (2013.01); *B01L 9/00* (2013.01); *C12M 23/28* (2013.01); *C12M 41/00* (2013.01); *C12M 41/46* (2013.01); *C12Q 1/02* (2013.01); *G01N 15/1456* (2013.01); *G01N 21/01* (2013.01); *G01N 21/17* (2013.01); *G01N 21/75* (2013.01); *G01N 2015/0065* (2013.01)

(58) Field of Classification Search
CPC ............. C12Q 1/02; G01N 2015/0065; G01N 21/359; G01N 15/06; G01N 15/1456; G01N 2015/0053; G01N 2015/0693; G01N 2021/0307; G01N 2021/0321; G01N 2021/0378; G01N 21/01; G01N 21/0303; G01N 21/17; G01N 21/75; B01L 9/00; C12M 23/28; C12M 41/00; C12M 41/46
USPC .......................................................... 250/341.2
See application file for complete search history.

(56) References Cited

U.S. PATENT DOCUMENTS

| | | | | |
|---|---|---|---|---|
| 5,329,936 A | * | 7/1994 | Lafferty | A61B 1/00096 600/109 |
| 6,001,066 A | * | 12/1999 | Canfield | G01J 5/0022 374/E13.003 |
| 6,123,454 A | * | 9/2000 | Canfield | G01J 5/02 374/158 |

(Continued)

*Primary Examiner* — David J Makiya
*Assistant Examiner* — Taeho Jo (57) ABSTRACT

An optical probe with associated disposable polymer sheath for near-infrared optical interrogation of fluids within bioprocessing vessels by means of transmission or transflection spectroscopy provides for the determination of quantities and parameters of substances in fluids contained within bioprocessing vessels. Associated methods for use of the optical probe and associated sheath to determine quantities of substances in fluids and parameters of fluids during bioprocesses are provided.

12 Claims, 4 Drawing Sheets

(51) Int. Cl.
*C12M 1/00* (2006.01)
*G01N 15/00* (2006.01)

(56) References Cited

U.S. PATENT DOCUMENTS

| | | | | |
|---|---|---|---|---|
| 6,137,108 A * | 10/2000 | DeThomas | ............... | G01J 3/42 |
| | | | | 250/339.07 |
| 6,270,494 B1 * | 8/2001 | Kovalcheck | ....... | A61B 1/00142 |
| | | | | 600/121 |
| 7,379,783 B2 | 5/2008 | Popp | | |
| 7,379,784 B2 | 5/2008 | Popp | | |
| 7,392,107 B2 | 6/2008 | Popp | | |
| 7,799,273 B2 | 9/2010 | Popp | | |
| 7,916,299 B2 * | 3/2011 | Trump | .................... | G01F 1/704 |
| | | | | 356/436 |
| 8,008,065 B2 * | 8/2011 | Selker | .................... | C12M 23/00 |
| | | | | 435/287.1 |
| 8,187,867 B2 | 5/2012 | Kunas et al. | | |
| 8,491,839 B2 | 7/2013 | Popp | | |
| 8,591,811 B2 | 11/2013 | Popp | | |
| 8,660,680 B2 | 2/2014 | Popp | | |
| 8,708,319 B2 | 4/2014 | Terentiev et al. | | |
| 9,008,815 B2 | 4/2015 | Popp | | |
| 9,092,028 B2 | 7/2015 | Popp | | |
| 9,195,228 B2 | 11/2015 | Popp | | |
| 2005/0283058 A1 * | 12/2005 | Choo-Smith | ........ | A61B 5/0088 |
| | | | | 600/315 |
| 2007/0107618 A1 * | 5/2007 | Lacroix | .................. | F41H 11/12 |
| | | | | 102/402 |
| 2008/0243031 A1 * | 10/2008 | Seibel | .................. | A61B 1/0008 |
| | | | | 600/566 |
| 2011/0124035 A1 * | 5/2011 | Broadley | ............... | C12M 41/00 |
| | | | | 435/29 |
| 2011/0160595 A1 * | 6/2011 | Stone | ................. | A61B 1/00142 |
| | | | | 600/474 |
| 2012/0244608 A1 * | 9/2012 | Selker | .................... | C12M 41/00 |
| | | | | 435/288.7 |
| 2013/0261368 A1 * | 10/2013 | Schwartz | ............ | A61N 5/1027 |
| | | | | 600/1 |
| 2014/0012155 A1 * | 1/2014 | Flaherty | ................ | A61B 5/015 |
| | | | | 600/549 |
| 2014/0260712 A1 * | 9/2014 | Damren | ................ | A61M 39/18 |
| | | | | 73/866.5 |
| 2014/0275986 A1 * | 9/2014 | Vertikov | ................ | A61B 5/061 |
| | | | | 600/424 |
| 2015/0297092 A1 * | 10/2015 | Irisawa | ................ | A61B 5/0095 |
| | | | | 600/407 |

* cited by examiner

NEAR-INFRARED OPTICAL PROBE AND ASSOCIATED DISPOSABLE SHEATH

CROSS-REFERENCE TO RELATED APPLICATIONS

This application claims the benefit of U.S. provisional patent application No. 61/992,735, filed May 13, 2014, for "Optical Interfaces for Bioprocessing Vessels." Such application is incorporated herein by reference in its entirety.

STATEMENT REGARDING FEDERALLY SPONSORED RESEARCH OR DEVELOPMENT

This invention was made with government support under grant no. 1353021 awarded by the National Science Foundation. The government has certain rights in this invention.

BACKGROUND

The present invention relates to near-infrared optical sampling means and methods for providing optical communication between an optical instrument and a fluid within a bioprocessing vessel for applications including, but not limited to, pharmaceutical manufacturing, food processing, and chemical manufacturing as well as other laboratory and industrial processes.

The use of optical and electronic instrumentation to monitor and control the contents of vessels and changes taking place therein is well known in the art. Processing and storage of, for example, food, beverage, chemical, agricultural, fuel, and pharmaceutical products has historically taken place primarily in multiple-use vessels comprised of stainless steel and/or glass. Numerous hardware approaches enabling interrogation and analysis of the contents of such vessels by, for example, optical, electronic, and electrochemical techniques have been described in the art. Dissolved oxygen may be measured by, for example, electrochemical probes with oxygen-permeable membranes, as well as fluorescent sensor techniques. Measurement of pH is possible by electrochemical techniques as well as fluorescent indicators. Probes for measurement of optical characteristics of materials in rigid vessels by transmission, reflection, and attenuated total reflection (ATR) are also known in the art. Such probes are often of tubular form and primarily metal construction, protruding through a head plate or side wall of a vessel and into the material under process. Such probes are typically in direct contact with the material under process. Probes and sensors of this general description are commonly designed for robustness and longevity—tolerating use, cleaning, and often sterilization for many process cycles. Such multiple-use probes and sensors typically have form factors that are not accommodating to interfacing with single-use bioreactors, particularly flexible bioreactors and those with small working volumes. Flexible bioreactors, also known as bag bioreactors, lack rigidity—surfaces commonly distort during operation, making attachment and positioning of typical multiple-use probes difficult and unstable. Bioreactors with small working volumes simply do not have the surface area or volume to support many of the sensors and probes that are common in the art. Moreover, such prior art sensors and probes do not commonly fit within the model of single-use technology as they are not disposable and must be in contact with the process fluid, thereby requiring the cleaning, sterilization, and aseptic insertion steps that single-use technology seeks to avoid.

Regular cleaning and maintenance of multiple-use vessels is required to maintain process integrity, and sterile conditions are often necessary, demanding yet more laborious and/or costly cleaning and disinfection procedures. The maintenance, cleaning, and disinfection of multiple-use process vessels coupled with the high initial cost of the equipment has led to accelerating adoption of single-use, disposable vessels in multiple industries. These single-use vessels are most commonly constructed of polymers, and are often purchased pre-sterilized such that the user may immediately put them to use. As such single-use vessels are most commonly pre-sterilized and ready for use, sensors are commonly integrated into the vessel before sterilization and sterilized with the vessel. Any sensors or connections to the vessel that are not integrated and sterilized with the vessel may be externally sterilized and installed via aseptic ports. While use of sensors or probes that are not installed into the vessel prior to sterilization of the vessel is feasible, it is typically undesirable due to the additional labor required of the end user as well as the increased probability of contamination. Such single-use vessels offer several additional benefits over conventional multiple-use bioreactors: ease of use; reduced setup labor for end users; significantly reduced cleanup time; and lower equipment costs. Single-use disposable bioreactors are available in a variety of sizes and form factors—working volumes range from sub-milliliter to thousands of liters.

A key aspect in bioprocessing is being able to transition processes from small-scale experiments in the research lab to a large-scale production environment. The research and effort to transition from small-scale experiments to production is known as scale-up, and this process is commonly challenging and time consuming. Scale-up often comprises three major phases—the research phase where initial studies are performed and processes are selected and verified; the pilot plant phase where processes are further studied, refined, and verified in higher volume processes; and the production phase where large-scale manufacturing is performed. The conditions present in small-volume research bioreactors may be markedly different from those present in the larger bioreactors in the pilot plant and on the production floor. Indeed, processes can vary considerably even between different bioreactors in the research lab. In order to execute the scale-up process in the most efficient manner possible, it is desirable to have the ability to optimize a plurality of process parameters and constituent concentrations, and often to be able to control such parameters and constituent concentrations. Ideally such monitoring and control capabilities will be uniform throughout the various stages of scale-up. Bioreactors having working volumes of microliters to few milliliters are commonly known as micro-bioreactors, and are often configured such that multiple micro-bioreactors are used to perform experiments in parallel. Such multiplexed experiments with cell culture or fermentation processes enable evaluation of process conditions, cell lines, or other variables in an efficient manner. So-called miniature-bioreactors commonly have working volumes of tens to few hundreds of milliliters, and offer another step in the scale-up process. Similarly to micro-bioreactors, mini-bioreactors are often configured in groups for parallel experimentation, though with a working volume that better represents more standard process conditions. Due to the larger form factor, mini-bioreactors may also offer enhanced process monitoring and control functionality over micro-bioreactors. While reliable monitoring of constituent concentrations of fluids in bioprocesses such as nutrient analyte concentrations remains challenging even in large-volume bioreactors, the challenge is amplified with micro- and mini-bioreactors given the space constraints and form factors. Sensor technologies capable of providing such analyte concentration information, and ideally control of such concentrations, in bioreactors used across the product development arc from research lab to production plant are desired in the biotechnology and pharmaceutical industries.

Sensors for measurement of a variety of parameters within single-use vessels have been demonstrated. Analysis of physical and chemical conditions such as pH and dissolved oxygen (DO) is possible by means of sensors comprising fluorescent indicators. Single-use and disposable temperature and pressure sensors have been demonstrated. Optical interfaces for vessels of polymeric construction, which may be single-use and/or flexible vessels, are also known in the art, though to a far lesser extent than similar interfaces for multiple-use vessels. Interfaces for transmission, reflection, and ATR optical measurements have been disclosed, however these interfaces and ports are generally not optimized for near-infrared spectroscopic applications. Numerous polymers are available that are at least partially transparent to visible and short-wave infrared (SWIR), though these polymers are often substantially opaque or exhibit significant absorption structure at wavelengths longer than 1.5 µm.

Bioreactors commonly require frequent monitoring and strict control in order to ensure adequate environmental and nutritional conditions for fermentation, cell cultures, or similar processes contained therein. While sensors are available to measure parameters such as DO and pH as is hardware and software to control these parameters, sensors and systems to monitor nutrients and analytes in an automated fashion and control the levels thereof have historically been largely absent in the art. This is the case for both multiple- and single-use bioreactors, however sensor solutions to interface with single-use bioreactors have been particularly lacking.

Measurement of nutrients and analytes by spectroscopic methods, particularly infrared spectroscopic methods, presents a robust means to monitor said nutrients and analytes and control levels thereof within bioreactors and process vessels in general. In order to optically interface with bioprocessing vessels and their contents, integrated and robust optical interface solutions are desired. These solutions may be substantially transparent in the wavelength range of interest, and offer high measurement stability and optical throughput. The requirement of material transparency is particularly challenging for infrared spectroscopy, principally near- and mid-infrared spectroscopy, where optical absorption by many commonly used polymers is unacceptably high when polymer thicknesses are within the satisfactory range to maintain mechanical integrity.

The trend towards adoption of single-use sensors and components in bioprocesses, including single-use bioprocessing vessels, is often at odds with sensor technologies that are necessarily complex. While sensors that are entirely disposable may be preferred, such approaches may not be feasible for certain sensing methods. An alternative to disposable sensors is sensors that utilize a disposable sheath or cover that provides a barrier between a non-disposable sensor and a bioprocess. If such a sheath or cover does not substantially hinder the sensing method, non-disposable sensors with disposable covers may perform advantageously in bioprocesses using both disposable and non-disposable bioprocessing vessels.

BRIEF SUMMARY

As used herein, the terms "optical" and "light" refer to electromagnetic radiation having vacuum wavelengths between 300-20,000 nm.

As used herein, "near infrared", "near-infrared", and "NIR" mean the region of the electromagnetic spectrum generally spanning wavenumbers between 3300 cm$^{-1}$ and 14,000 cm$^{-1}$ (corresponding to wavelengths of approximately 0.7 µm to 3.0 µm).

As used herein, "interrogation" and "sampling" mean illuminating a sample with optical radiation and collecting at least a portion of the radiation having interacted with said sample for optical analysis.

As used herein, "constituent" means a chemical analyte, protein, DNA, component in a fluid, cell, or solid suspended in a fluid.

The present invention relates to a near-infrared optical probe using a disposable polymer sheath for determining quantities of substances and parameters in fluids within bioprocessing vessels. Embodiments of the present invention provide a polymer sheath comprising at least portions that are substantially transparent to near-infrared electromagnetic radiation, and wherein at least portions of the polymer sheath are compressible such that an optical path length may be defined by compression of the polymer sheath by elements on the optical probe. The disposable polymer sheath provides a fluid impermeable barrier between a near-infrared optical probe and a fluid contained within a bioprocessing vessel. In this manner, an optical probe may comprise mechanically robust materials such as metals and glasses as well as a plurality of optical elements. While such mechanical and optical complexity would be undesirable in a disposable optical probe, it is acceptable in a non-disposable hardware configuration. The use of a disposable sheath with the non-disposable probe combines the robustness and proven manufacturing techniques of non-disposable technology with the convenience of disposable sensors.

Methods are also provided for performing near-infrared optical measurements in a bioprocessing vessel using said disposable sheath and non-disposable optical probe. Quantities of substances such as alcohols, sugars, lipids, organic acids, peptides, steroidal molecules, and proteins may be determined by performing near-infrared spectroscopic measurements with embodiments of the present invention optical probe and disposable polymer sheath. Measurements of cell density, cell viability, and turbidity may also be performed in bioprocesses with embodiments of the present invention. The present invention may be configured in a variety of bioprocessing vessels, and may provide optical interrogation during a storage stage, a growth stage, a product formation stage, a purification stage, or a formulation stage.

The detailed description and drawings provided herein will offer additional scope to certain implementations of the present invention. It should be understood that the described implementations are provided as examples only. Those skilled in the art will recognize that numerous variations and modifications of the described implementations are within the scope of the invention.

DETAILED DESCRIPTION

Figure 1:
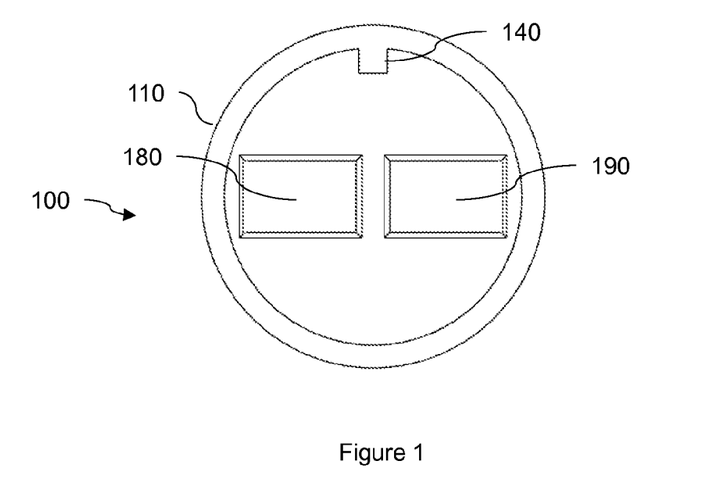
FIG. 1 shows a top view of a disposable polymer sheath for an optical probe.
Figure 2:
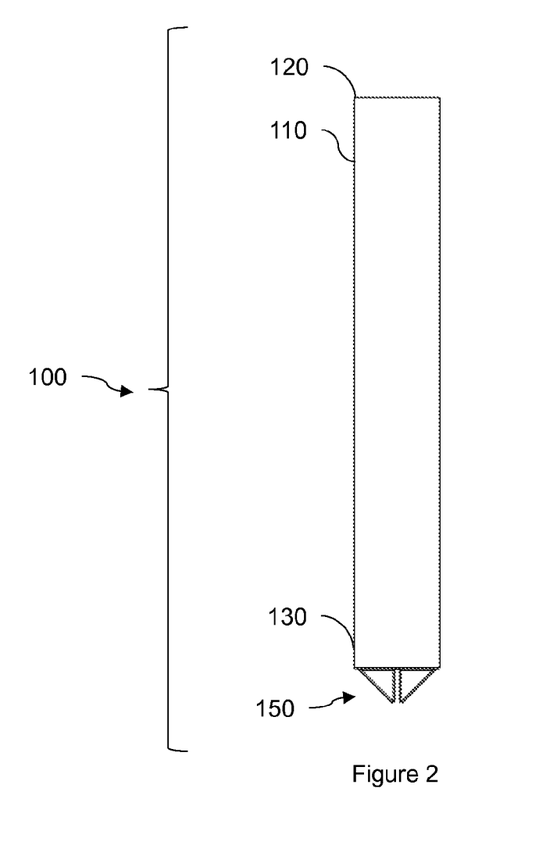
FIG. 2 shows a side view of a disposable polymer sheath for an optical probe.

A top view of an embodiment of the present invention disposable polymer sheath is shown in FIG. 1 and a corresponding side view is shown in FIG. 2. In one embodiment, the disposable sheath 100 comprises a hollow tubular member 110 having an open end 120 configured to be positioned outside of a bioprocessing vessel and a closed end 130 configured to be positioned within the fluid contained in a bioprocessing vessel. The open end 120 is configured to receive an optical probe, and the hollow tubular member 110 and closed end 130 and configured to provide a fluid impermeable barrier between the contents of the bioprocessing vessel and an optical probe. In some embodiments, the disposable polymer sheath 100 may provide a hermetic seal between the bioprocessing vessel contents and the exterior of the bioprocessing vessel. The described fluid impermeable barrier is desirable to ensure that the contents of the bioprocessing vessel are not exposed to conditions outside of the bioprocessing vessel such that the vessel contents are not contaminated.

Figure 3:
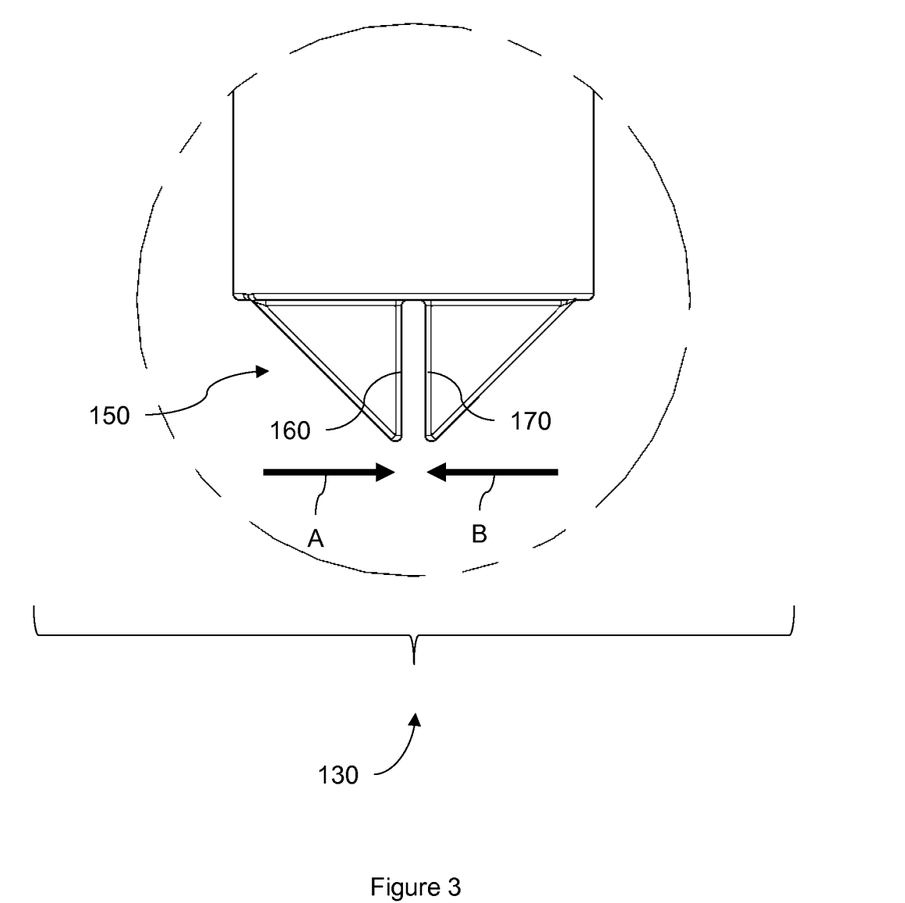
FIG. 3 shows a detailed view of the optical sampling region of a disposable polymer sheath for an optical probe.

Embodiments of the present invention provide an optical sampling region 150 within the closed end 130 of the disposable polymer sheath 100, shown in the side view of FIG. 2. The optical sampling region 150 comprises one or more features to receive optical elements on an optical probe. A side view in FIG. 3 shows additional detail near the closed end 150 of the disposable polymer sheath 100. The optical sampling region 150 comprises a first surface 160 and a second surface 170 that are generally opposing. At least portions of said first 160 and second 170 surfaces in the optical sampling region will desirably be at least partially transparent to near-infrared electromagnetic radiation. The region between the first 160 and second 170 surfaces in the optical sampling region 150 provides an optical path length through the fluid within a bioprocessing vessel.

Due to the fact that many polymers exhibit strong absorption features in certain wavelength ranges of the electromagnetic spectrum, it may be advantageous that any polymers used in the first 160 and second 170 surfaces in the optical sampling region 150 that are within the optical beam path be selected to minimize such absorption. For example in the near-infrared wavelength range of the electromagnetic spectrum (comprising wavenumbers between 3300 cm−1 and 5600 cm−1), strong absorption features may arise from C—H, C—O, O—H, and N—H chemical bonds. For this reason it may be preferable to use polymers lacking such chemical bonds in the optical sampling regions of disposable bioprocessing vessels designed for optical interrogation by such wavelengths. Perfluorinated polymers such as Teflon® polytetrafluoroethylene (PTFE), ethylene tetrafluoroethylene (ETFE), Teflon® fluorinated ethylene propylene (FEP), Teflon® amorphous fluoroplastics (AF), and Teflon® perfluoroalkoxy copolymer (PFA) lack the listed chemical bonds and thus may be preferable for polymer materials within the optical path. Alternatively, other polymer materials may be used if sufficiently thin to provide adequate optical transmission in the desired wavelength range. For example, polycarbonate being less than 0.25 mm in thickness may offer satisfactory optical transmission in the near-infrared wavelength range.

Disposable bioprocessing vessels are commonly provided to end users pre-sterilized so that end users may immediately put the products to use. It is also desirable that components and sensors used within disposable bioprocessing vessels to monitor bioprocesses are compatible with sterilization techniques, and that such components and sensors are sterilized with the vessel. Sterilization of vessels and associated components and sensors together reduces contamination risks by minimizing handling and exposure of the components to non-sterile air and environments. Materials used for construction of embodiments of the present invention will preferably be amenable to sterilization by one or more of gamma irradiation, beta irradiation, ethylene oxide gas, or autoclave. It is also desirable that materials chosen for construction of embodiments of the present invention will be FDA and/or USP Class VI compliant after sterilization. As embodiments of the present invention may be configured to operate in non-disposable bioprocessing vessels that are typically sterilized by steam or autoclave, it is desirable that such embodiments are tolerant of steam and autoclave sterilization. The Teflon® family of products described above, including fluorinated ethylene propylene (FEP), are particularly suitable to embodiments of the present invention due to their high temperature tolerance (commonly service temperatures meet or exceed 200° C.) combined with low optical absorption in the near-infrared wavelength range of the electromagnetic spectrum. The ability to injection mold FEP makes it particularly attractive to producing single-use components for bioprocessing applications utilizing near-infrared sensors.

In certain embodiments of the present invention, shown in FIG. 1, the closed end 130 of the disposable polymer sheath 100 comprises a first compartment 180 and a second compartment 190 to receive optical elements. Said first compartment 180 comprises said first surface 160, and said second compartment 190 comprises said second surface 170. Optical elements on an optical probe may be received in said first 180 and second 190 optical compartments to provide optical communication through a fluid within a bioprocessing vessel, wherein said fluid is optically interrogated between the first 160 and second 170 surfaces. In embodiments of the present invention, it is desirable that portions of the optical sampling region 150 are at least partially compressible. Appropriate polymers and thickness of said polymers will preferably be selected to comprise the optical sampling region 150 such that sufficient flexibility and compressibility of the polymers is provided where the position of the first surface 160 may be moved in the direction of arrowed line A in FIG. 3 by an optical element installed in the first compartment 180. Similarly, the flexibility of the polymers in the optical sampling region 150 will provide for the position of the second surface 160 to be moved in the direction of arrowed line B by an optical element installed within the second compartment 190. By compressing the first surface 160 in the direction of arrowed line A and the second surface 170 in the direction of arrowed line B, a defined optical path length through the fluid may be provided by compression. The merits of establishing an optical path length by compression of polymer components have been established in U.S. patent application Ser. No. 14/631,914, the teachings of which are incorporated by this reference. Defining an optical path length by compression of polymer elements may be used advantageously in the optical sampling of fluids. The use of rigid optical and mechanical materials such as metallic and glass elements to provide compression surfaces that act to deform a polymer element or elements to a desired shape or to have a desired distance between two or more elements may provide a highly stable optical path length. Embodiments of the present invention provide for optical path lengths through a fluid of 0.5 mm to 2.0 mm, inclusively. This range of optical path lengths through a fluid is desirable for near-infrared optical spectroscopic applications in aqueous fluids.

Figure 4:
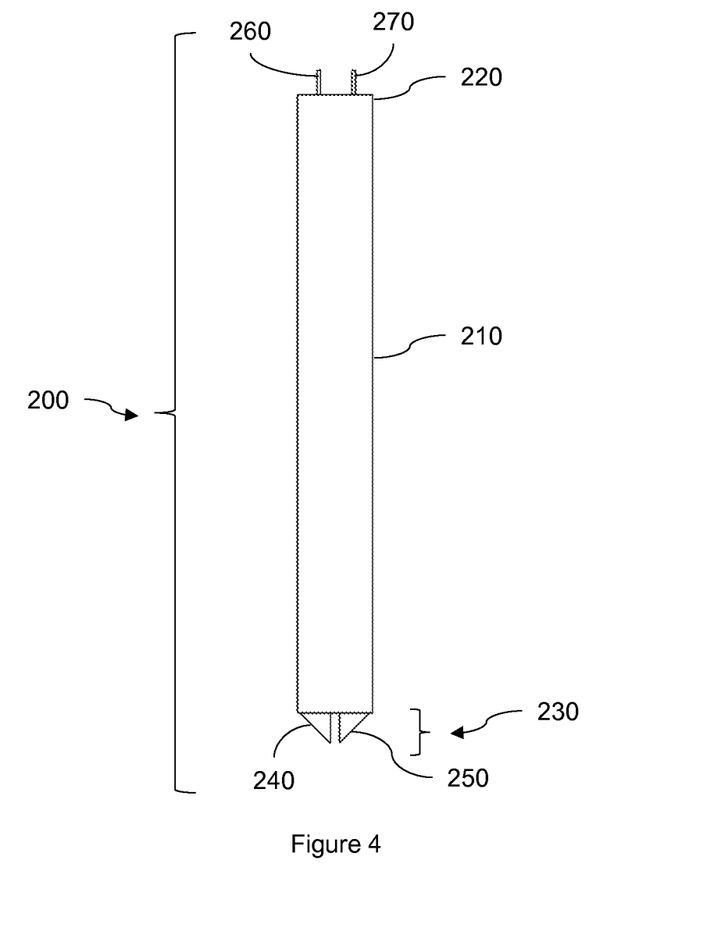
FIG. 4 shows a side view of an optical probe for use with a disposable polymer sheath.

Embodiments of the present invention provide for an optical probe to be used in conjunction with the disposable polymer sheath 100. A side view of such an optical probe is shown in FIG. 4. The optical probe 200 comprises a hollow tubular body 210 having a first end 220 being exterior to a bioprocessing vessel and a second end 230 being interior to a bioprocessing vessel and configured to be installed within a disposable polymer sheath 100. The second end comprises a first optical element 240 and second optical element 250 that are configured to establish an optical path therebetween when installed within the disposable polymer sheath 100. A first optical waveguide 260 is provided for optical communication with the first optical element 240 and a second optical waveguide 270 for optical communication with the second optical element 250.

Figure 5:
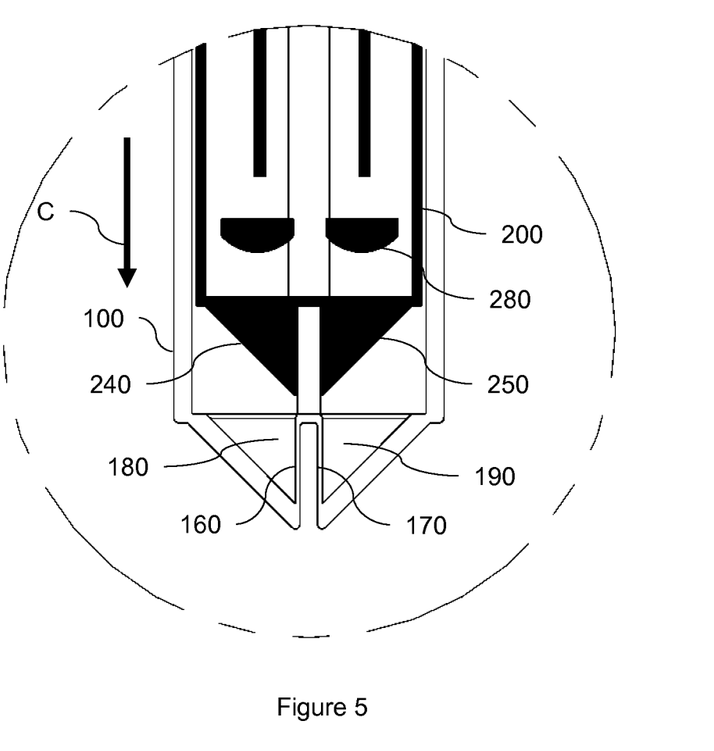
FIG. 5 shows a detailed sectional view of an optical probe partially installed within a disposable polymer sheath.

The detailed sectional view in FIG. 5 shows an optical probe 200 partially installed in a disposable polymer sheath 100. To install an optical probe 200 within a disposable polymer sheath 100, the optical probe is translated in the direction of arrowed line C until the optical elements 240 and 250 are seated within the corresponding compartments 180 and 190. The distance between the opposing surfaces on the first 240 and second 250 optical elements on the optical probe 200 is preferably configured to be smaller than that between the inside of the first surface 160 and second surface 170 in the optical sampling region 150 of the disposable polymer sheath 100 such that the optical elements 240 and 250 compress at least portions of the first 160 and second 170 surfaces towards each other. The action of compressing at least portion of the first 160 and second 170 surfaces defines an optical path length therebetween. The optical probe 200 may further comprise additional optical elements 280 to improve optical throughput or otherwise alter the spatial or spectral characteristics of electromagnetic radiation being communicated by the probe 200. Embodiments of the present invention optical probe 200 configured for operation in near-infrared wavelengths of the electromagnetic spectrum will preferably comprise optical components being substantially transparent at the desired wavelengths. Certain embodiments will desirably comprise optical waveguides 260 and 270 that are optical fibers providing low optical losses. Examples of materials that may be used to construct such optical fibers include low-OH silica-clad-silica, chalcogenide glass, indium fluoride ($InF_3$), and zirconium fluoride ($ZrF_4$). These materials are known to provide low optical losses in a substantial portion of the near-infrared wavelength range of the electromagnetic spectrum.

Figure 6:
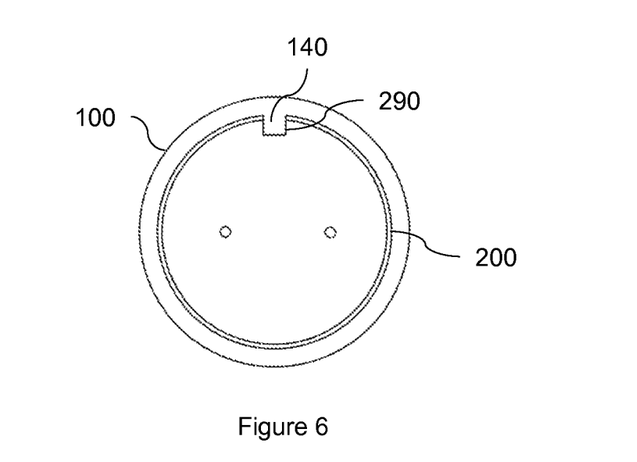
FIG. 6 shows a top view of an optical probe partially installed within a disposable polymer sheath.

For optical sampling in spectroscopic applications, it is desirable that accurate positioning is provided between the optical probe 200 and disposable polymer sheath 100. An alignment feature 290 on the optical probe 200 is shown in FIG. 6, and is desirably provided to engage with the alignment feature 140 on the disposable polymer sheath 100. Such alignment features provide orientation of the probe 200 and disposable polymer sheath 100 relative to each other, and also provide for proper seating of the optical elements 240 and 250 within the first 180 and second 190 compartments that are configured to receive said optical elements.

Methods are provided for performing near-infrared optical measurements in bioprocessing vessels with embodiments of the present invention disposable polymer sheath 100 and optical probe 200. A disposable polymer sheath 100 comprising compressible features is first installed in a bioprocessing vessel. The bioprocessing vessel may be a single-use or a multiple-use bioprocessing vessel. Examples of single-use bioprocessing vessels include rigid polymer vessels, bag bioprocessing vessels, and miniature bioprocessing vessels. Connection to any vessel will desirably be a fluid impermeable connection to ensure isolation of the fluid inside the bioprocessing vessel from the exterior of the vessel. Such a fluid impermeable connection to a polymer vessel may be formed by for example adhesive bonding, thermal welding, ultrasonic welding, or by compression. Connections to multiple-use bioprocessing vessels such as bioreactors comprising metal and/or glass components may be provided by compression or by bonding to another polymer member that is used as a fixture for installation of the disposable polymer sheath.

An optical probe 200 is then installed within the disposable polymer sheath 100, and optical or mechanical features on the optical probe 200 are used to compress partially compressible features on the disposable polymer sheath to provide a defined optical path length in a fluid contained within a bioprocessing vessel. Certain embodiments of the present invention provide for an optical path length through a fluid in a bioprocessing vessel defined by compression between 0.5 mm and 2.0 mm, inclusively. Near infrared electromagnetic radiation from an optical instrument may be communicated to the optical probe 200 where it is communicated to the fluid within a bioprocessing vessel. At least a portion of the near-infrared electromagnetic radiation having interacted with the fluid in a bioprocessing vessel is communicated by the optical probe to an optical instrument where one or more quantities of substances contained within the fluid may be determined.

Embodiments of the present invention and corresponding methods provide for communication of near-infrared electromagnetic radiation between an optical instrument and the optical probe 200 installed within the disposable polymer sheath 100. Optical spectroscopy with near-infrared electromagnetic radiation offers a plurality of advantages for determining quantities of substances in fluids. Optical absorption features in the 3300 $cm^{-1}$ to 5600 $cm^{-1}$ wavenumber range are often present for substances having C—H, O—H, C—O, N—H, S—H, and P—H chemical bonds, offering the possibility to determine quantities of substances containing such chemical bonds using near-infrared spectroscopy. While water is sufficiently strongly absorbing in several wavelength ranges throughout the infrared electromagnetic spectrum to limit the effectiveness of transmission or transflection spectroscopic techniques to determine quantities of substances, the 3300 $cm^{-1}$ to 5600 $cm^{-1}$ wavenumber range provides a water transmission window centered at approximately 4600 $cm^{-1}$. In this wavenumber range the water absorption is sufficiently low to allow adequate optical throughput through fluid samples with a sufficiently short optical path length to determine quantities of substances by spectroscopic techniques. In order to provide sufficient optical throughput through a fluid and also provide a satisfactory optical path length for interaction of electromagnetic radiation with the fluid, optical path lengths through fluids ranging from 0.5 mm to 2.0 mm are preferable for embodiments of the present invention. Measurements with near-infrared spectroscopic techniques may be used to determine quantities of substances in fluids such as alcohols, sugars, lipids, organic acids, peptides, and steroidal molecules as such substances often comprise optical absorption features at near-infrared wavelengths due to their chemical bonds. In addition to measurements of optical absorption by transmission or transflection measurement approaches to determine quantities of substances by their absorption spectra, near-infrared spectroscopic techniques may be used to determine parameters such as cell density, cell viability, or turbidity. Due to the reduction in optical scattering with increasing wavelength, optical path lengths between 0.5 mm and 2.0 mm may be used even when conducting high cell density bioprocesses such as *Pichia pastoris* fermentations. Use of wavenumbers higher than 5600 cm$^{-1}$ (shorter wavelength than 1.8 µm) often requires short path lengths or operation with low cell density applications due to the increased optical scattering encountered and resulting optical attenuation.

Embodiments of the present invention may be provided for determining quantities of substances in a plurality of stages of bioprocessing. It is often desirable to perform monitoring of quantities of substances within fluids during several stage of bioprocessing. Monitoring during static stages such as product storage may be used for example to determine whether a product is stable. Monitoring during dynamic stages such as a growth stage may be used to track the quantities of substances in fluids as a function of time, and also to enable control of the quantities of substances. For example, carbon sources may be monitored during a growth stage, and feedback control used to maintain desired levels of one or more of such carbon sources. The present invention provides configurations for determining quantities of substances in fluids during storage, growth, product formation, product purification, and product formulation stages. Embodiments of the present invention may be provided for processes such as batch processes as well as continuous processes such as perfusion processes. Downstream processes such as product purification may also utilize embodiments of the present invention for determination of constituents in fluids.

The present invention has been described with reference to the foregoing specific implementations. These implementations are intended to be exemplary only, and not limiting to the full scope of the present invention. Many variations and modifications are possible in view of the above teachings. The invention is limited only as set forth in the appended claims. All references cited herein are hereby incorporated by reference to the extent not inconsistent with the disclosure herein. Unless explicitly stated otherwise, flows depicted herein do not require the particular order shown, or sequential order, to achieve desirable results. In addition, other steps may be provided, or steps may be eliminated, from the described flows, and other components may be added to, or removed from, the described systems. Accordingly, other implementations are within the scope of the following claims. Any disclosure of a range is intended to include a disclosure of all ranges within that range and all individual values within that range.

The invention claimed is:

1. A disposable polymer sheath for receiving an optical probe in a bioprocessing vessel, said disposable polymer sheath comprising:
   a hollow tubular member for installation into a bioprocessing vessel, said hollow tubular member comprising an open end exterior to the bioprocessing vessel for receiving an optical probe, a closed end interior to the bioprocessing vessel, a sidewall, and an alignment feature configured to orient an optical probe within said hollow tubular member, and wherein the hollow tubular member is impermeable to fluid within the bioprocessing vessel;
   an optical sampling region comprising at least two opposing surfaces, at least a portion of said surfaces comprising a polymer being at least partially optically transparent to near-infrared electromagnetic radiation;
   wherein at least a portion of said optical sampling region is at least partially compressible whereby an optical path length is formed by compression.

2. The disposable polymer sheath of claim 1, wherein said disposable polymer sheath comprises fluorinated ethylene propylene (FEP).

3. The disposable polymer sheath of claim 1, wherein said portion of said optical sampling region being compressible and forming an optical path length through the fluid of between 0.5 mm and 2.0 mm inclusively.

4. The disposable polymer sheath of claim 1, wherein said disposable polymer sheath is suitable for sterilization by one or more of gamma irradiation, beta irradiation, ethylene oxide, or autoclave.

5. The disposable polymer sheath of claim 1, wherein said polymer is at least partially transparent to near-infrared electromagnetic radiation comprising wavenumbers between 3300 cm$^{-1}$ and 5600 cm$^{-1}$.

6. The disposable polymer sheath of claim 1, further comprising an optical probe, wherein said optical probe comprises:
   a tubular body comprising a first end exterior to the bioprocessing vessel and a second end interior to the bioprocessing vessel, said second end comprising a first optical element and a second optical element, said first and second optical elements positioned to establish an optical path therebetween;
   a first optical waveguide and a second optical waveguide configured to provide optical communication between an instrument and said first and second optical elements;
   an alignment feature for aligning said optical probe with the polymer hollow tubular member;
   wherein said first and second optical elements are configured to be positioned within the hollow tubular member and are configured to compress said at least partially compressible portion of the optical sampling region to define an optical path length;
   wherein said optical probe is fluidically isolated from the contents of the bioprocessing vessel by the hollow tubular member.

7. The disposable optical sheath of claim 6, wherein said first and second optical elements are configured to compress features of the hollow tubular member to provide an optical path length through the fluid between 0.5 mm and 2.0 mm inclusively.

8. The disposable optical sheath of claim 6, wherein said first and second optical waveguides comprise optical fibers comprising a material selected from the group consisting of low-OH silica, chalcogenide glass, zirconium fluoride (ZrF$_4$), and indium fluoride (InF$_3$).

9. A method for performing optical measurements in a bioprocessing vessel using an optical probe and associated polymer sheath, said method comprising the steps:
   installing a polymer sheath for an optical probe within the bioprocessing vessel, wherein the sheath comprises at least partially compressible features configured to receive optical elements located on the optical probe;
   installing an optical probe within said polymer sheath;
   compressing said at least partially compressible features to provide a defined optical path length in a fluid sample contained within said bioprocessing vessel;
   communicating near-infrared electromagnetic radiation from an optical instrument into said optical probe;
   collecting at least a portion of near-infrared electromagnetic radiation having interacted with the contents of a bioprocessing vessel and communicating at least a portion of said electromagnetic radiation to said an optical instrument;

determining with said optical instrument one or more quantities of substances in the fluid sample contained within said bioprocessing vessel.

10. The method of claim 9, wherein said step of determining with said optical instrument one or more quantities of substances in a fluid sample comprises the step of measuring one or more of alcohols, sugars, lipids, organic acids, peptides, steroidal molecules, or proteins in the fluid sample.

11. The method of claim 9, wherein said step of determining with said optical instrument one or more quantities of substances in a fluid sample comprises the step of measuring one or more of cell density, cell viability, or turbidity in the fluid sample.

12. The method of claim 9, wherein said step of determining with said optical instrument one or more quantities of substances in a fluid sample is performed during a bioprocess selected from the group consisting of a growth stage, a product formation stage, a purification stage, a storage stage, and a product formulation stage.

* * * * *